United States Patent
Lee

(10) Patent No.: US 11,202,896 B2
(45) Date of Patent: Dec. 21, 2021

(54) HAND GESTURE BASED TATTOO MACHINE CONTROL

(71) Applicant: TCM Supply Corporation, City of Industry, MI (US)

(72) Inventor: Rock Lee, City of Industry, CA (US)

(73) Assignee: TCM Supply Corporation, City of Industry, CA (US)

( * ) Notice: Subject to any disclaimer, the term of this patent is extended or adjusted under 35 U.S.C. 154(b) by 1070 days.

(21) Appl. No.: 15/699,362

(22) Filed: Sep. 8, 2017

(65) Prior Publication Data

US 2019/0076636 A1   Mar. 14, 2019

(51) Int. Cl.
| | | |
|---|---|---|
| *A61M 37/00* | (2006.01) | |
| *G06F 3/01* | (2006.01) | |
| *G05B 15/02* | (2006.01) | |

(52) U.S. Cl.
CPC ......... *A61M 37/0076* (2013.01); *G05B 15/02* (2013.01); *G06F 3/017* (2013.01); *A61M 2205/3569* (2013.01); *A61M 2205/505* (2013.01); *A61M 2205/8206* (2013.01); *G05B 2219/36133* (2013.01)

(58) Field of Classification Search
CPC ..... G05B 15/02; G06F 3/017; A61M 37/0076
See application file for complete search history.

(56) References Cited

U.S. PATENT DOCUMENTS

| | | |
|---|---|---|
| 6,550,356 B1 | 4/2003 | Underwood |
| 8,723,668 B1 | 5/2014 | Strohallen et al. |
| 2011/0270358 A1 | 11/2011 | Davis et al. |
| 2013/0009875 A1 | 1/2013 | Fry et al. |
| 2013/0096599 A1 | 4/2013 | Colton |
| 2015/0335175 A1 | 11/2015 | Choueifati et al. |
| 2016/0164519 A1* | 6/2016 | Arriaga ............... H03K 17/945 606/186 |
| 2017/0049524 A1* | 2/2017 | Olson .................... G06F 3/014 |

FOREIGN PATENT DOCUMENTS

| | | |
|---|---|---|
| FR | 3009500 | 2/2015 |
| WO | WO-2015156715 A1 * | 10/2015 ........ A61M 37/0076 |

* cited by examiner

*Primary Examiner* — John W Poos
(74) *Attorney, Agent, or Firm* — Quinn IP Law

(57) ABSTRACT

A system for controlling a tattoo machine configured to push ink includes a computerized processor configured to control a voltage supplied to the tattoo machine. The computerized processor includes programming configured to monitor a hand gesture input, determine a desired command for the tattoo machine based upon the monitored hand gesture input, and control the voltage supplied to the tattoo machine based upon the determined desired command. Monitoring the hand gesture input can include monitoring a touch-free hand gesture sensor.

16 Claims, 10 Drawing Sheets

HAND GESTURE BASED TATTOO MACHINE CONTROL

TECHNICAL FIELD

This disclosure is related to control of a tattoo machine, and, in particular, is related to controlling voltage applied to a tattoo machine based upon hand gestures made to a control panel.

BACKGROUND

The statements in this section merely provide background information related to the present disclosure. Accordingly, such statements are not intended to constitute an admission of prior art.

Tattoo machines push ink into the skin of a person. The appearance of the ink is controlled by a voltage applied to the tattoo machine. Different voltages can be required for line work versus shade work. Voltages can be controlled based upon knobs, scalar up and down buttons, and/or foot pedal controls.

SUMMARY

A system for controlling a tattoo machine configured to push ink includes a computerized processor configured to control a voltage supplied to the tattoo machine. The computerized processor includes programming configured to monitor a hand gesture input, determine a desired command for the tattoo machine based upon the monitored hand gesture input, and control the voltage supplied to the tattoo machine based upon the determined desired command. Monitoring the hand gesture input can include monitoring a touch-free hand gesture sensor.

BRIEF DESCRIPTION OF THE DRAWINGS

One or more embodiments will now be described, by way of example, with reference to the accompanying drawings, in which.

DETAILED DESCRIPTION

Figure 1:
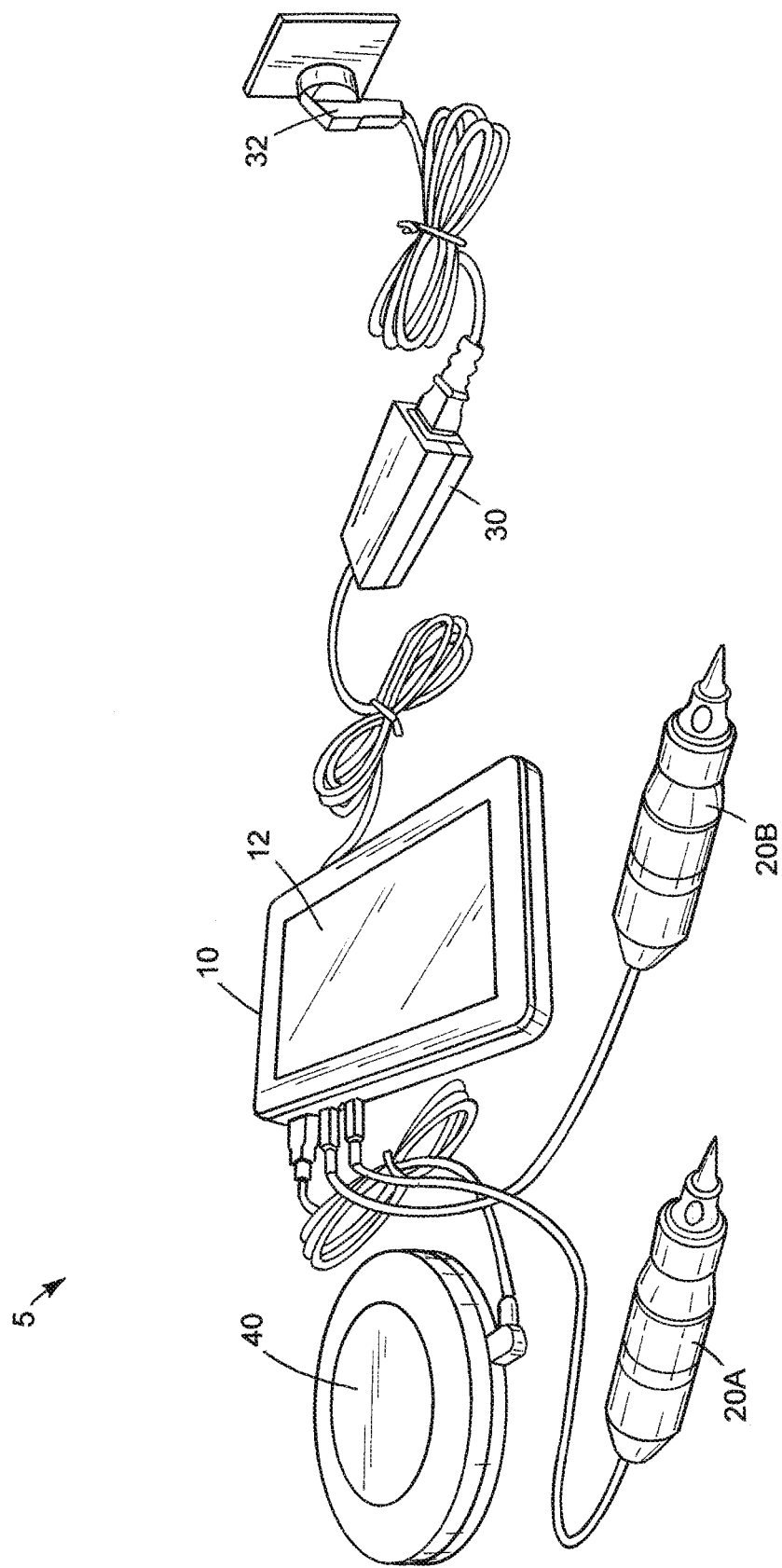
FIG. 1 illustrates an exemplary tattoo machine control system, in accordance with the present disclosure.

Referring now to the drawings, wherein the showings are for the purpose of illustrating certain exemplary embodiments only and not for the purpose of limiting the same, FIG. 1 illustrates an exemplary tattoo machine control system. Exemplary tattoo machine control system 5 includes a computerized control unit 10, power supply 30, tattoo machines 20A and 20B, and optional floor foot switch 40. Tattoo machines 20A and 20B are devices known in the art including a needle, a supply of ink, and excitation means for moving the needle in a way effective to push ink into the skin of a person. Machines 20A and 20B can be controlled by a voltage provided to the machines by control unit 10. Different voltage magnitudes result in different behavior of the tattoo machines 20A and 20B, and tattoo machines 20A and 20B can be different from each other to give the tattoo artist an ability to achieve different tattoo effects. Exemplary power supply 30 is attached to a known electrical wall outlet at plug 32. Floor foot pedal 40 is optional and enables the user to achieve different results, such as alternating power on/power off, based upon a foot input to floor foot pedal 40. Floor foot pedal 40 can be attached to control unit 10 with electronic wiring, or floor foot pedal 40 can be connected wirelessly with control unit 10 through exemplary Bluetooth® or other similar connection methods.

Any number of tattoo machines can be controlled by the disclosed system, for example, including one tattoo machine or four tattoo machines.

Control unit 10 can be any electronic device capable of receiving inputs from a user in accordance with the disclosure. Control unit is provided herein as a generic term for any such device, and it will be understood that the control unit can be described, in certain embodiments, as any of a power supply control display, a power supply control panel, or a power supply display. In one embodiment, control unit 10 can include a smart phone. In another embodiment, control unit 10 can include a tablet device. In another embodiment, control unit 10 can include a dedicated device including a display and one or more sensors configured to monitor hand inputs by the user. Control unit 10 can include computerized components capable of executing programming or stored commands, or control unit 10 can be electronically connected to a remote device, system, or server capable of executing programming or stored commands.

Control unit 10 of FIG. 1 includes a processor configured to operate a computerized process to control the voltage applied to tattoo machines 20A and 20B. Control unit 10 can include a smart phone, a tablet computer, a laptop computer, or any other similar device. Control unit 10 includes user interface 12. User interface 12 can include a touch screen device, enabling liquid crystal display (LCD) or similar graphics display and input through touch finger contact to the screen of the user interface 12. Additionally or alternatively, user interface 12 can include a camera, infrared sensors, or other similar known sensor devices to receive input including a hand gesture near to but not touching the screen of the device. Such sensors configured to monitor a hand gesture without the hand of the user actually touching the screen of the device are known in the art and are generally referred to herein as touch-free hand gesture sensors.

Tattoo machines are known in the art and include electromagnetic coils which provide an excitation force to move an armature bar up and down. A needle is connected to the armature bar and is used to push ink into the skin of the person getting the tattoo. The voltage provided by the described control unit of the disclosure controls excitation of the electromagnetic coils. A tattoo as described herein can include any type of artwork or design created within the skin of a person. According to this disclosure, permanent make-up is considered a type of tattoo, and the processes and systems described herein can be used to create tattoos and permanent makeup.

Figure 7:
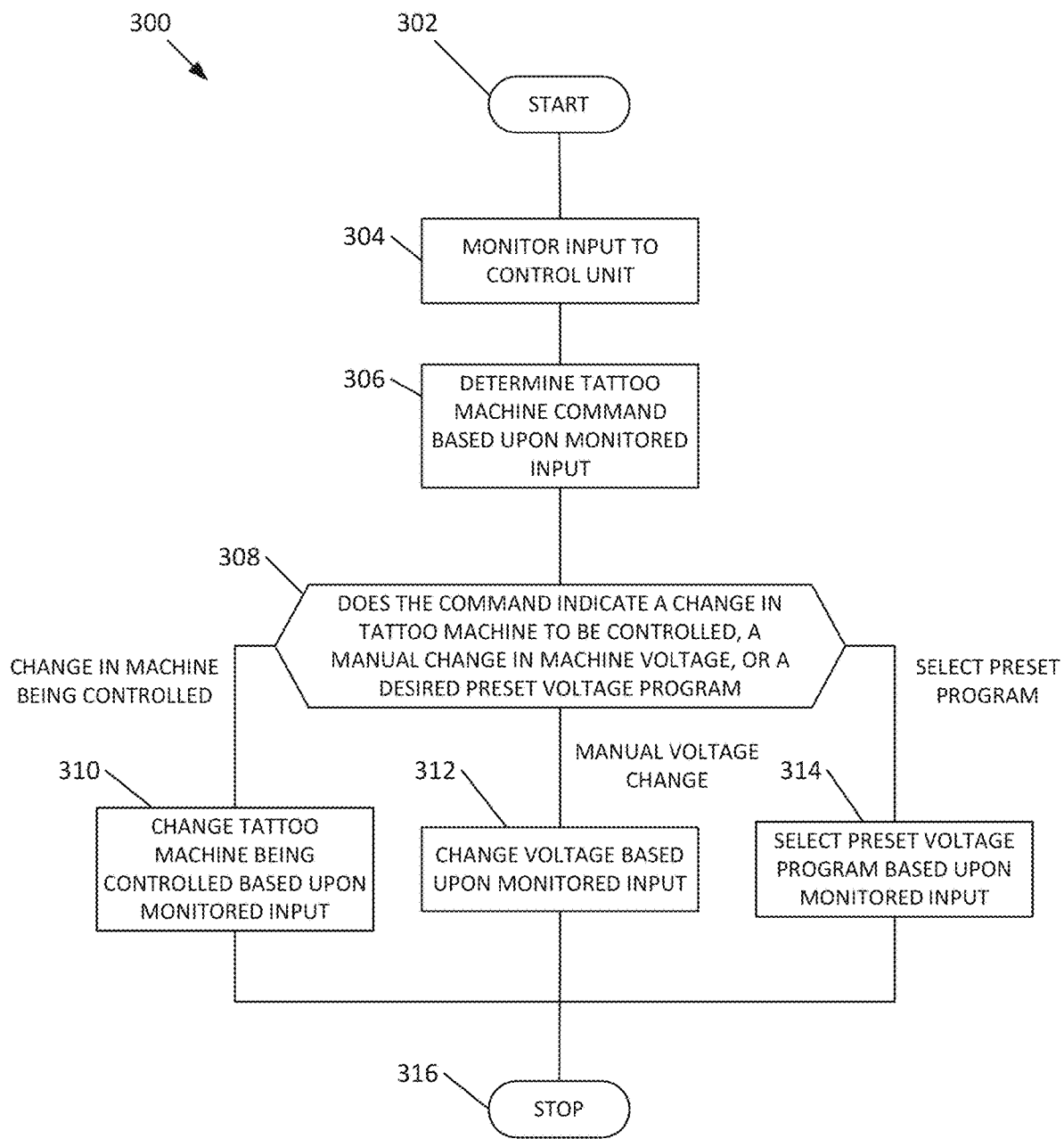
FIG. 7 illustrates through a flow chart exemplary operation of the tattoo machine control system of FIG. 1, in accordance with the present disclosure.

A process is disclosed for operating the tattoo machine control system of FIG. 1, wherein hand gestures can be monitored, either through a touch screen device or through a touch-free hand gesture sensor, and a tattoo machine connected to the system is controlled based upon the monitored hand gesture. FIG. 7 illustrates through a flow chart exemplary operation of the tattoo machine control system of FIG. 1. Process 300 starts at step 302. At step 304, the system monitors a user hand gesture input to the control unit. At step 306, the system determines a tattoo machine command based upon the monitored user hand gesture input. At step 308, the system determines whether the tattoo machine command includes one of 1) a desired change in machine being controlled, 2) a manual change in voltage, or 3) desired selection of a preset voltage program, for example, picking a particular preselected voltage. At step 310, the system changes tattoo machine being controlled (e.g., between tattoo machines 20A and 20B of FIG. 1) based upon the monitored input. At step 312, the system changes voltage applied to a connected tattoo machine based upon a manual input setting, for example, increasing or decreasing incrementally based upon a hand gesture indicated by the user. At step 314, the system selects a preset voltage program based upon the monitored input. At step 316 the process ends. The process can run iteratively, enabling one to keep making inputs and controlling tattoo machines through continuous operation of the machines. Process 300 is exemplary, and any number of variations to the process are envisioned.

Figure 2:
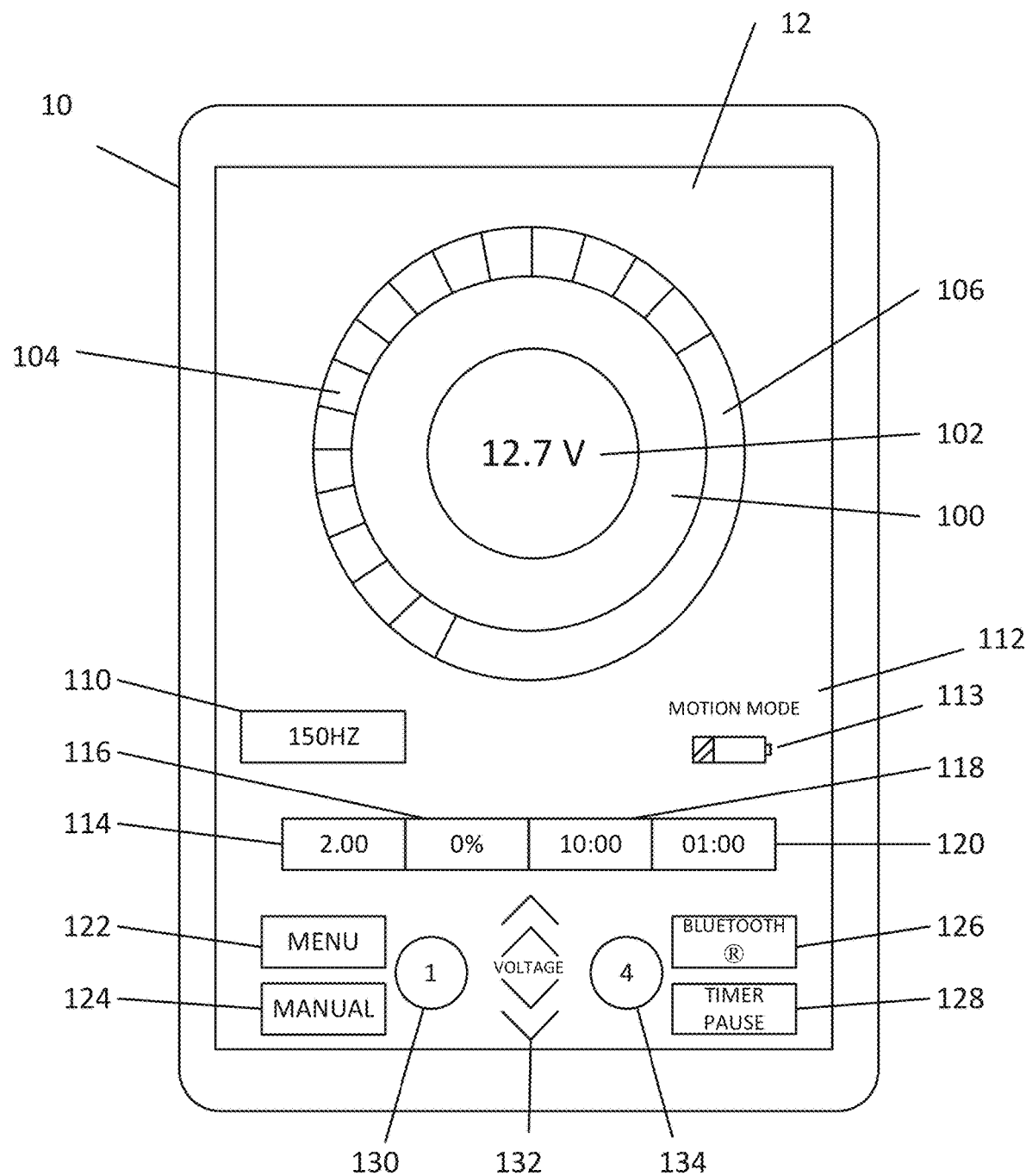
FIG. 2 illustrates an exemplary display for the control unit of FIG. 1, in accordance with the present disclosure.

FIG. 2 illustrates an exemplary display for the control unit of FIG. 1. Control unit 10 includes user interface 12 comprising an LCD or similar display. The unit can include a touch screen enabled screen and/or sensors enabling touch-free hand gesture inputs. A number of visual controls are illustrated upon user interface 12. A voltage display and selection graphic 100 is illustrated including a numeric voltage display 102, a scalar circular display 104 which increases in size, range, or illumination based upon varying voltage selections, and exemplary empty scalar circular display 106 which illustrates for the user how much more the voltage can be increased. Any number of visual displays can be utilized enabling a user to interpret how the voltage output of the control unit is being changed, graphic 100 is exemplary, and the disclosure is not intended to be limited to the examples provided.

Additionally, user interface 12 includes a control frequency 110 for the connected tattoo machine, an input mode indicator 112 (i.e., indication of which types of input are enabled), a battery level indicator 113, a current reading 114 describing a current draw for the connected tattoo machine, a duty cycle indication 116 for the tattoo machine (a term known in the art including an indication of how long a front spring touches a contact screw), clock 118, a timer 120, an options menu button 122, a user's manual display button 124, a Bluetooth® control button 126, a timer pause button 128, a tattoo machine selection button 130, a preset voltage program selection button 134, and a manual voltage change selector 132. The various buttons can be selected and controlled based upon touch screen input. Additionally, some of the features can be controlled by hand gesture input to the user interface 12. A number of specific hand gestures are disclosed herein as examples. Any number of hand gestures can be programmed originally with the control unit or trained to the control unit by the user, and the disclosure is not intended to be limited to the specific hand gesture inputs disclosed herein.

Figure 3A:
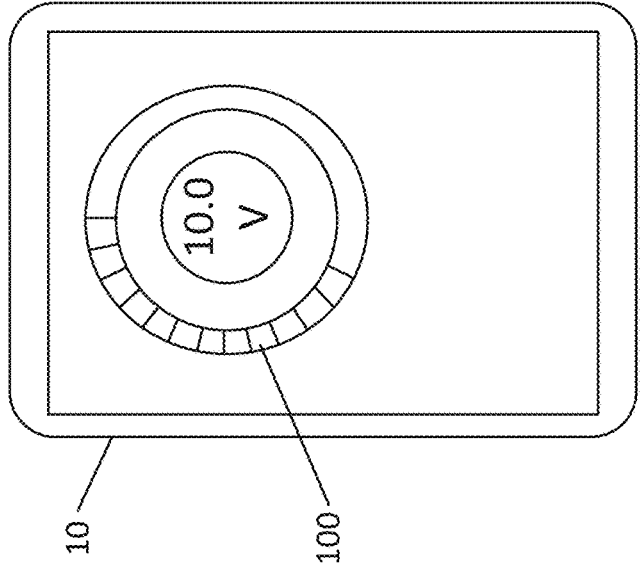
FIGS. 3A-3C illustrates an exemplary first hand gesture control for the control unit of FIG. 2, the user selecting a voltage for a controlled tattoo machine, in accordance with the present disclosure.
Figure 3B:
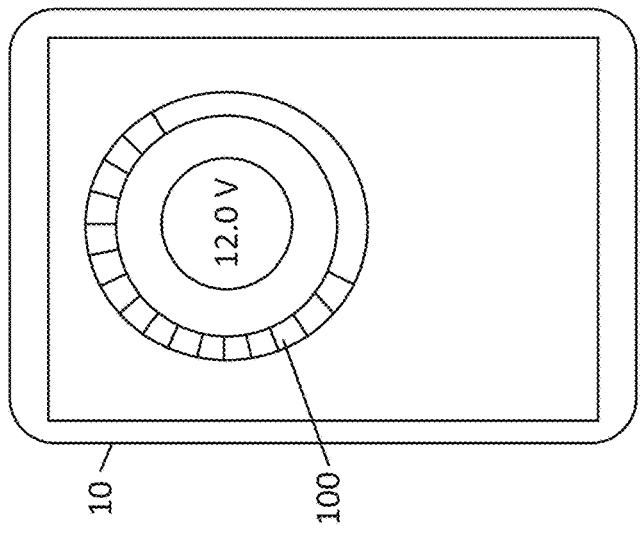
Figure 3B:
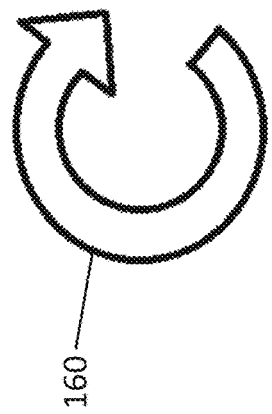
Figure 3C:
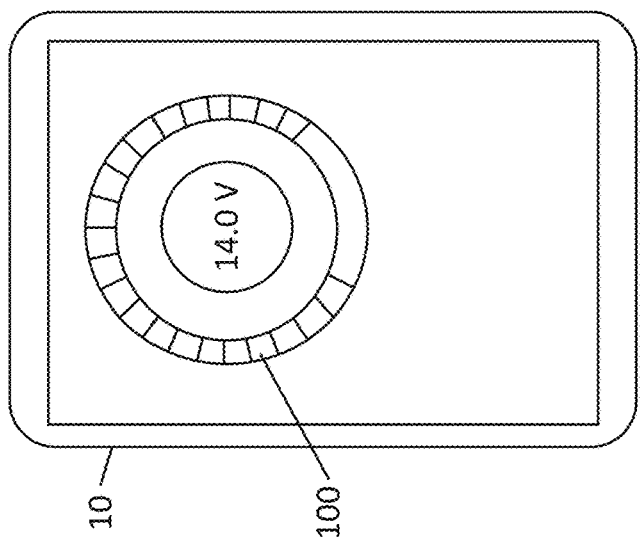

FIGS. 3A-3C illustrates an exemplary first hand gesture control for the control unit of FIG. 2, the user selecting a voltage for a controlled tattoo machine. In FIG. 3A, control unit 10 is illustrated, including voltage display and selection graphic 100 showing a first control voltage. In FIG. 3B, a hand gesture input 150 is illustrated showing a hand motion in a clockwise circle. Control unit 10 is illustrated, including voltage display and selection graphic 100 showing a control voltage elevated from the first control voltage of FIG. 3A. In FIG. 3C, a hand gesture input 160 is illustrated showing a second hand motion in a clockwise circle. Control unit 10 is illustrated, including voltage display and selection graphic 100 showing a control voltage elevated further from the control voltage of FIG. 3B. It will be appreciated that a hand gesture in a counter-clockwise motion can similarly incrementally decrease the voltage. The increments of increase and decrease can be preset by the manufacturer or set by the user.

Figure 4C:
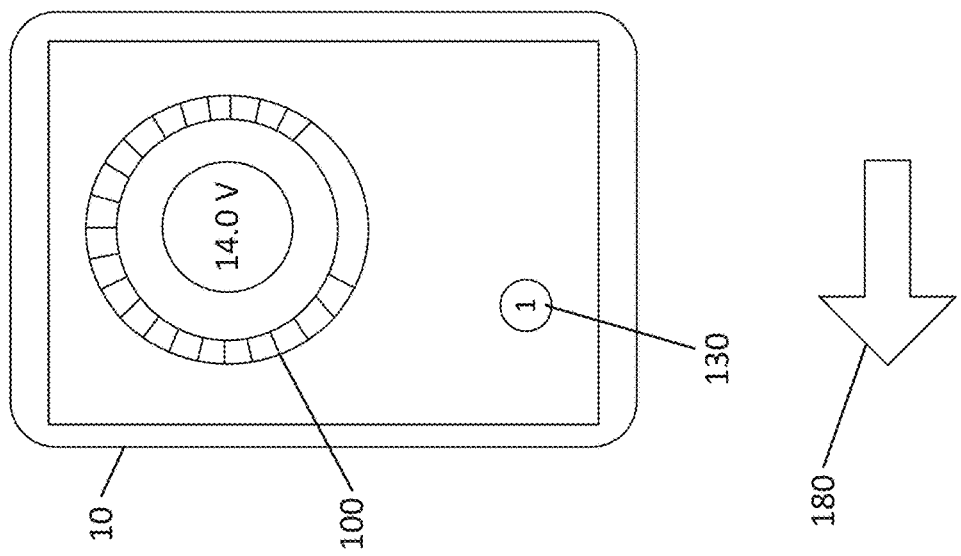
FIG. 4A-4C illustrates an exemplary second hand gesture control for the control unit of FIG. 2, the user selecting between two connected tattoo machines for control, in accordance with the present disclosure.
Figure 4B:
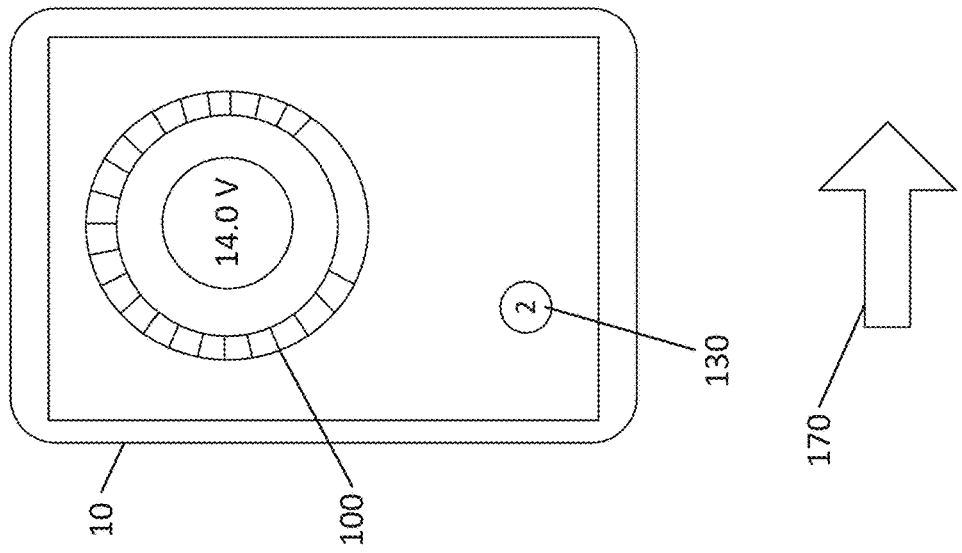
Figure 4A:
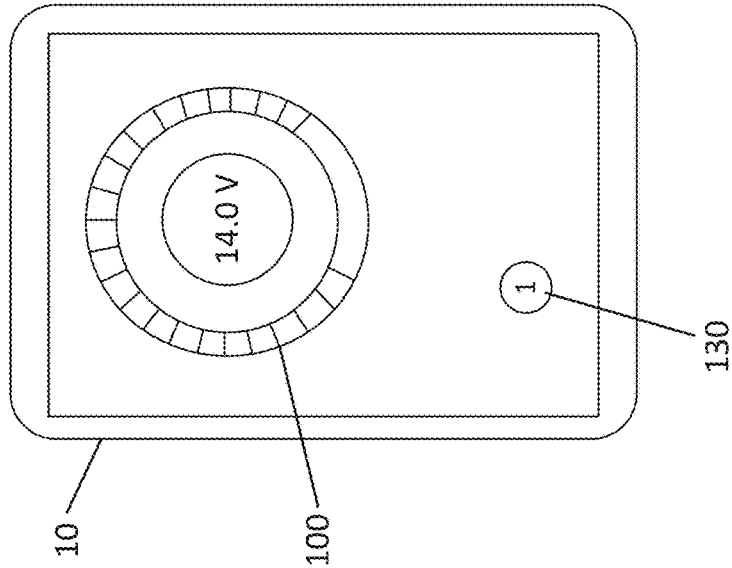

FIG. 4A-4C illustrates an exemplary second hand gesture control for the control unit of FIG. 2, the user selecting between two connected tattoo machines for control. In FIG. 4A, control unit 10 is illustrated, including voltage display and selection graphic 100 and a tattoo machine selection button 130, showing that a tattoo machine #1 is presently being controlled. In FIG. 4B, a hand gesture input 170 is illustrated showing a hand motion in a sweeping right motion. Control unit 10 is illustrated, including voltage display and selection graphic 100 and tattoo machine selection button 130, showing that as a result of the sweeping right motion input, the control unit has changed to control a tattoo machine with a greater number, tattoo machine #2. In FIG. 4C, a hand gesture input 180 is illustrated showing a second hand motion in a sweeping left motion. Control unit 10 is illustrated, including voltage display and selection graphic 100 and tattoo machine selection button 130, showing that as a result of the sweeping left motion input, the control unit has changed to control a tattoo machine with a lesser number, back to tattoo machine #1. Changing control from a first tattoo machine to a second tattoo machine can be described as commanding the first tattoo machine to deactivate and activating the second tattoo machine.

Figure 5C:
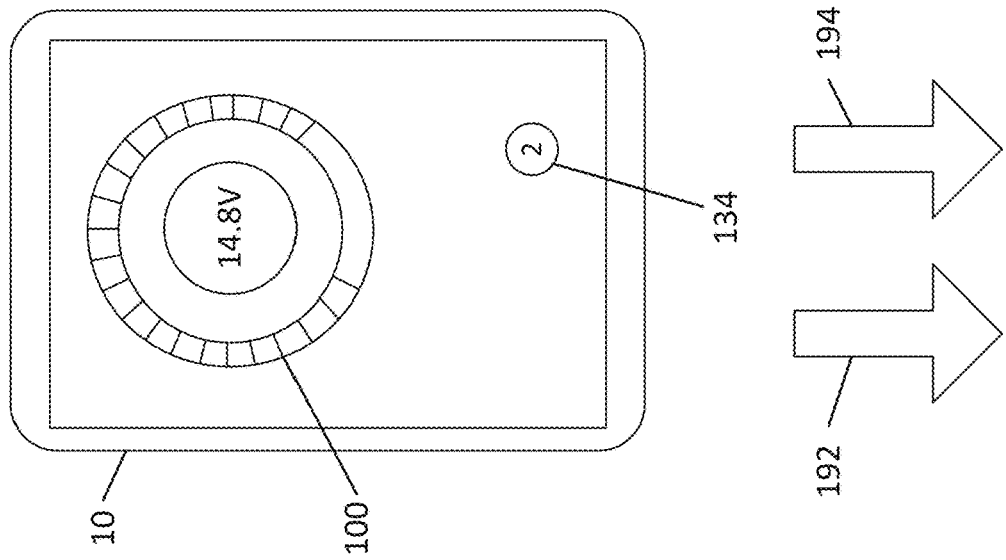
FIG. 5A-5C illustrates an exemplary third hand gesture control for the control unit of FIG. 2, the user selecting a voltage control preset program for a controlled tattoo machine, in accordance with the present disclosure.
Figure 5B:
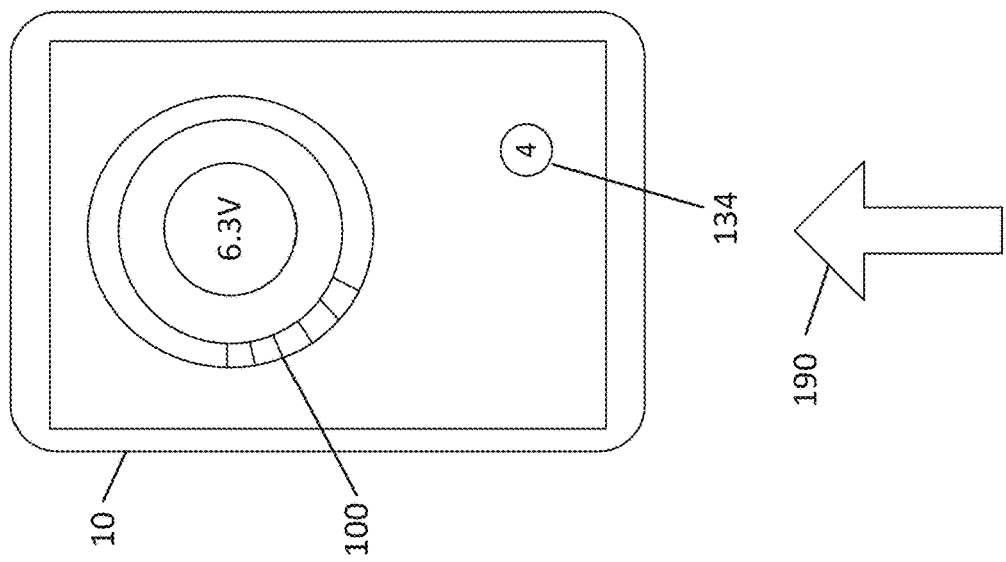
Figure 5A:
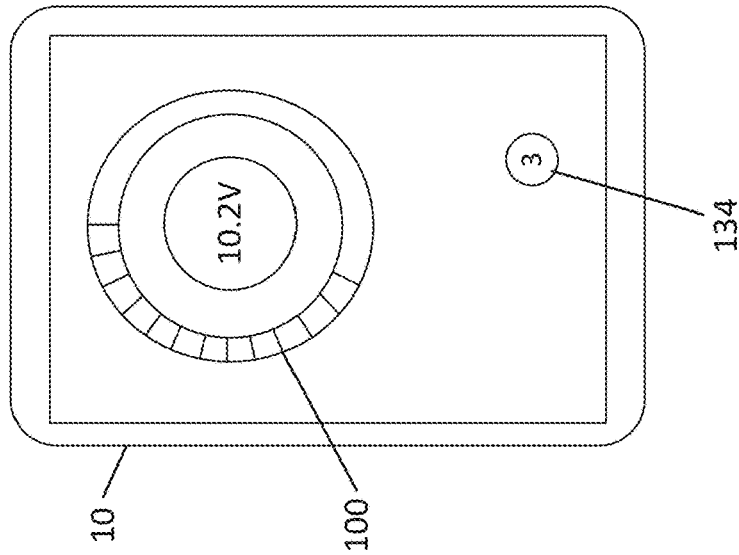

FIG. 5A-5C illustrates an exemplary third hand gesture control for the control unit of FIG. 2, the user selecting a voltage control preset program for a controlled tattoo machine. In FIG. 5A, control unit 10 is illustrated, including voltage display and selection graphic 100 and a preset voltage program selection button 134, showing that a voltage preset program #3 is presently being run. In FIG. 5B, a hand gesture input 190 is illustrated showing a hand motion in a sweeping up motion. Control unit 10 is illustrated, including voltage display and selection graphic 100 and preset voltage program selection button 134, showing that as a result of the sweeping up motion input, the control unit has changed to a voltage preset program with a greater number,

4. In FIG. 4C, a hand gesture inputs 192 and 194 are illustrated showing two consecutive hand motions in a sweeping down motion, indicating a desire of the user to decrease the preset voltage program number by two. Control unit 10 is illustrated, including voltage display and selection graphic 100 and preset voltage program selection button 134, showing that as a result of the two sweeping down motion inputs, the control unit has changed to a voltage preset program with a number two lesser than the number in FIG. 5B or #2.

The hand gestures of FIGS. 3A-3C, 4A-4C, and 5A-5C are exemplary. Any number of hand gestures can be used, and the disclosure is not intended to be limited to the examples provided herein. In one embodiment, the hand gestures can include a confirmation prompt to execute the change in voltage to avoid mistakes or errors in control. For example, a hand gesture in a clockwise motion can be used to indicate a desired increase in voltage. Upon monitoring such an input, the control unit can display "INCREASE VOLTAGE? SAY 'YES.'" The control unit can then implement or ignore the hand gesture based upon receiving confirmation. In another embodiment, confirmation can include monitoring the same input twice in a row. For example, upon monitoring a hand gesture in as a clockwise motion, the control unit can display "INCREASE VOLTAGE? REPEAT HAND GESTURE." The control unit can then implement or ignore the hand gesture based upon receiving confirmation. Any number of confirmation inputs can be used, and the disclosure is not intended to be limited to the particular examples provided herein.

Figure 6:
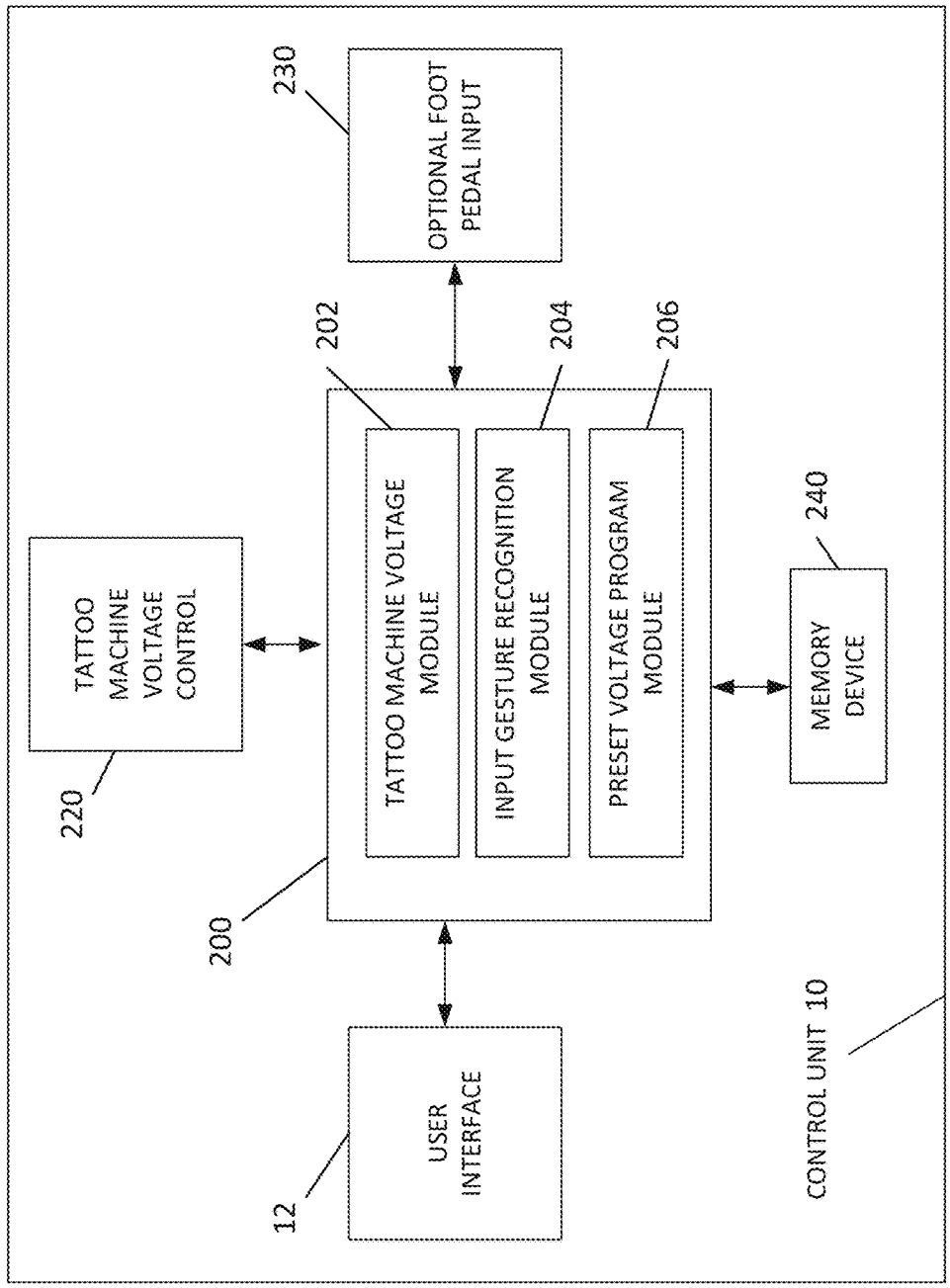
FIG. 6 schematically illustrates operation of the control unit of FIG. 2, in accordance with the present disclosure.

FIG. 6 schematically illustrates operation of the control unit of FIG. 2. Control unit 10 includes a processing device 200, a user interface 12, a tattoo machine voltage control 220, an optional foot pedal input 230, and a memory device 240.

The processing device 200 can include memory, e.g., read only memory (ROM) and random access memory (RAM), storing processor-executable memory (ROM) and random access memory (RAM), storing processor-executable instructions and one or more processors that execute the processor-executable instructions. In embodiments where the processing device 200 includes two or more processors, the processors can operate in a parallel or distributed manner. In the illustrative embodiment, the processing device 200 can execute an operating system of a portable computerized device, for example, when the control unit 10 is embodied as a tablet computer. In the illustrative embodiment, the processing device 200 also executes a tattoo machine voltage module 202, an input gesture recognition module 204, and preset voltage program module 206, which are described in greater detail below.

The user interface 12 is a device that allows a user to interact with the control unit. While one user interface 12 is shown, the term "user interface" can include, but is not limited to, a touch screen, a physical keyboard, a mouse, a microphone, and/or a speaker. As previously described, the user interface 12 can include sensors configured to monitor a hand gesture without the hand of the user actually touching the screen of the device. The foot pedal input 230 is a device that allows the control unit to communicate with and receive inputs from an optional foot pedal input device. The memory device 240 is a device that stores data generated or received by the control unit. The memory device 240 can include, but is not limited to, a hard disc drive, an optical disc drive, and/or a flash memory drive.

Tattoo machine voltage module 202 includes programming and/or hardware configured to operate programming which is configured to provide controls for the purpose of controlling and adjusting the voltage of one or more connected tattoo machines. Input gesture recognition module 204 includes programming and/or hardware configured to operate programming which is configured to monitor or receive inputs from a user, process the inputs according to protocols such as image recognition software, compare those inputs to defined gestures that are assigned to tattoo machine control commands, and determine a desired tattoo machine control command based upon the comparison. Preset voltage program module 206 includes programming and/or hardware configured to operate programming which is configured to store and operate preset voltage control programs. Such programs can include a static voltage magnitude or varying voltage magnitude programs such as periodic voltage pulses, sinusoid-shaped voltage curves, or similar periodic changes in voltage.

Figure 8:
FIG. 8 illustrates through a photograph an exemplary display in accordance with the embodiment of FIG. 2, in accordance with the present disclosure.

FIG. 8 illustrates through a photograph an exemplary display in accordance with the embodiment of FIG. 2.

Figure 9:
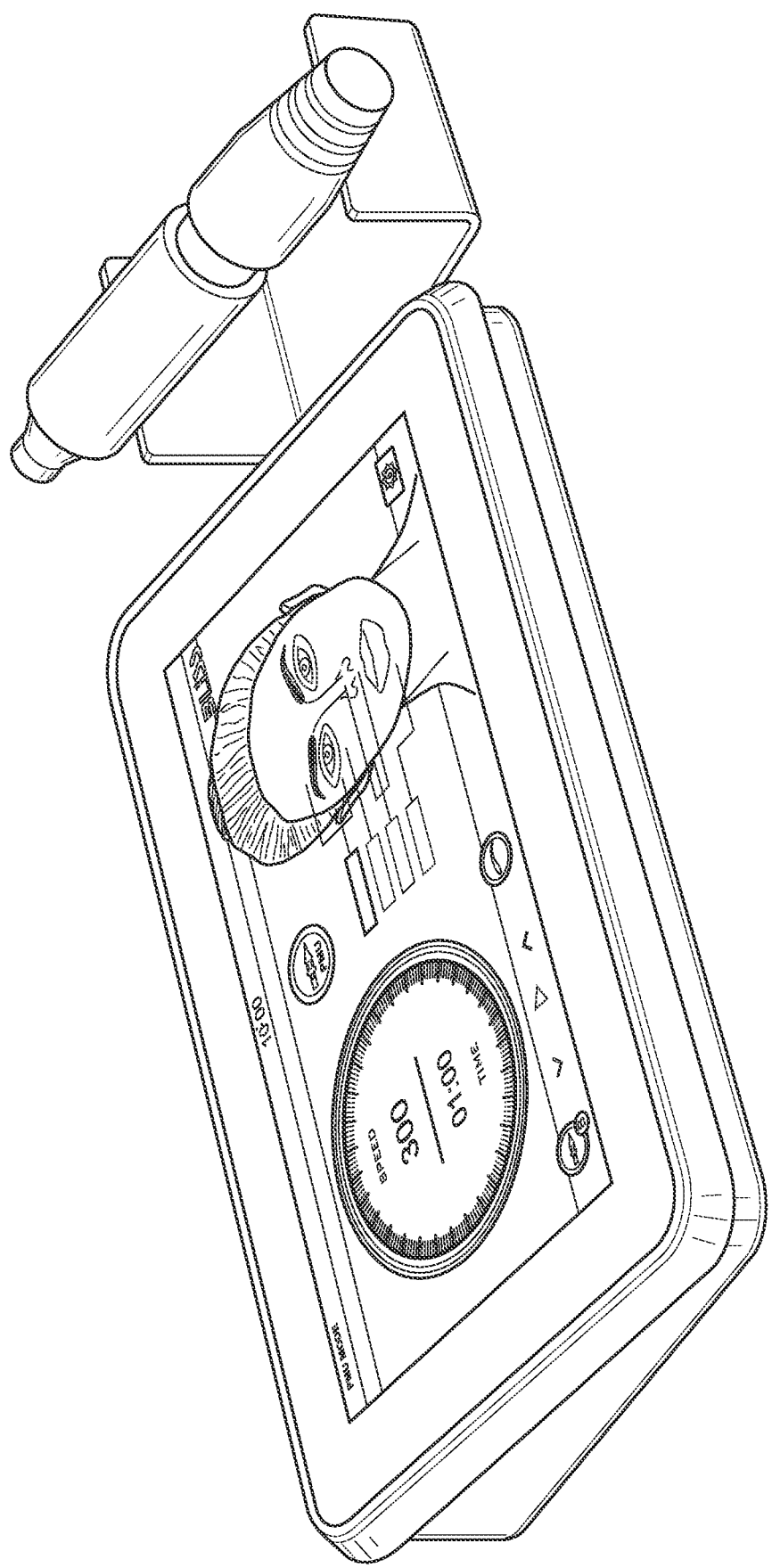
FIG. 9 illustrates through a photograph an alternative exemplary embodiment of the disclosed system, configured to control creation of permanent makeup, in accordance with the present disclosure.
Figure 10:
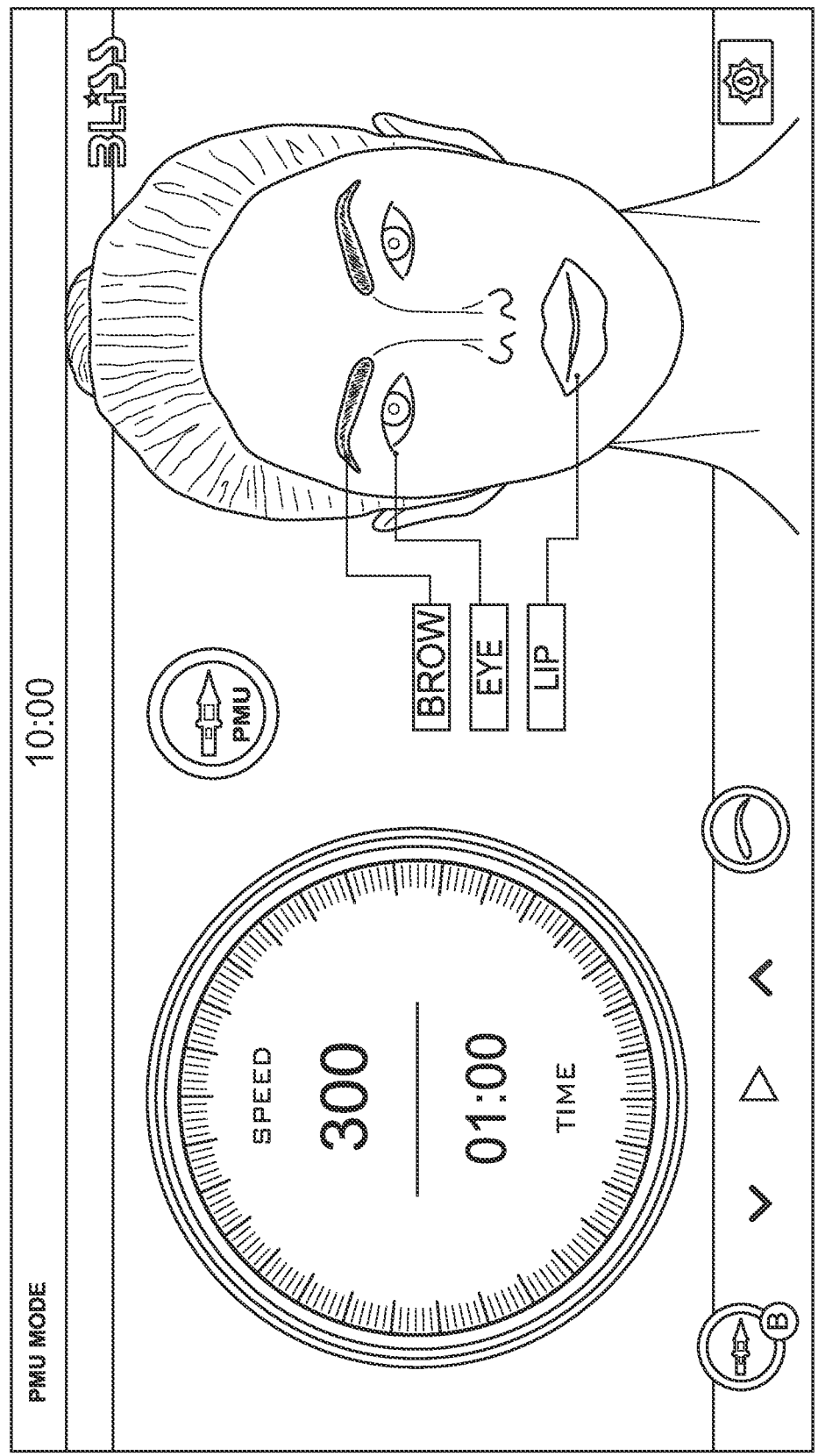
FIG. 10 illustrates through a photograph the embodiment of FIG. 9 in greater detail, in accordance with the present disclosure.

FIG. 9 illustrates through a photograph an alternative exemplary embodiment of the disclosed system, configured to control creation of permanent makeup. FIG. 10 illustrates through a photograph the embodiment of FIG. 9 in greater detail.

The photographs of FIGS. 8-10 are intended as non-limiting examples of display characteristics of the system of the disclosure.

The disclosure has described certain preferred embodiments and modifications of those embodiments. Further modifications and alterations may occur to others upon reading and understanding the specification. Therefore, it is intended that the disclosure not be limited to the particular embodiment(s) disclosed as the best mode contemplated for carrying out this disclosure, but that the disclosure will include all embodiments falling within the scope of the appended claims.

The invention claimed is:

1. A system for controlling a tattoo machine configured to push ink, comprising:
a computerized processor configured to control a voltage supplied to the tattoo machine, with programming configured to:
monitor a hand gesture input;
determine a desired command for the tattoo machine based upon the monitored hand gesture input; and
control the voltage supplied to the tattoo machine based upon the determined desired command; and
wherein the tattoo machine comprises a first tattoo machine; and
wherein determining the desired command for the tattoo machine comprises determining a desired command to deactivate the first tattoo machine and activate a second tattoo machine.

2. The system of claim 1, wherein monitoring the hand gesture input comprises monitoring a touch-free hand gesture sensor.

3. The system of claim 1, wherein determining the desired command for the tattoo machine comprises determining a desired command to incrementally change the voltage supplied to the tattoo machine.

4. The system of claim 1, wherein determining the desired command for the tattoo machine comprises determining a desired command to operate a preset voltage program.

5. The system of claim 1, wherein the tattoo machine is configured to create permanent makeup.

6. The system of claim 1, wherein monitoring the hand gesture input comprises monitoring a hand gesture in a clockwise motion.

7. The system of claim 1, wherein monitoring the hand gesture input comprises monitoring a hand gesture in a counter-clockwise motion.

8. The system of claim 1, wherein monitoring the hand gesture input comprises monitoring a hand gesture in a left-right motion.

9. The system of claim 1, wherein monitoring the hand gesture input comprises monitoring a hand gesture in an up-down motion.

10. The system of claim 1, wherein the computerized processor further includes programming to:
monitor a confirmation to the monitored hand gesture input; and
control the voltage supplied to the tattoo machine further based upon the monitored confirmation.

11. A system for controlling a tattoo machine configured to push ink, comprising:
a computerized processor configured to control a voltage supplied to the tattoo machine, with programming configured to:
monitor a hand gesture input
determine a desired command for the tattoo machine based upon the monitored hand gesture input
control the voltage supplied to the tattoo machine based upon the determined desired command;
monitor inputs to a floor foot pedal; and
provide control to the tattoo machine based upon the inputs to the floor foot pedal; and
wherein determining the desired command for the tattoo machine comprises determining a desired command to incrementally change the voltage supplied to the tattoo machine.

12. The system of claim 11, wherein monitoring the hand gesture input comprises monitoring a touch-free hand gesture sensor.

13. The system of claim 11, wherein determining the desired command for the tattoo machine further comprises determining a desired command to operate a preset voltage program.

14. The system of claim 11, wherein the tattoo machine is configured to create permanent makeup.

15. A system for controlling a tattoo machine configured to push ink, comprising:
a computerized processor configured to control a voltage supplied to the tattoo machine, with programming configured to:
monitor a hand gesture input
determine a desired command for the tattoo machine based upon the monitored hand gesture input
control the voltage supplied to the tattoo machine based upon the determined desired command;
monitor inputs to a floor foot pedal; and
provide control to the tattoo machine based upon the inputs to the floor foot pedal; and
wherein monitoring the hand gesture input comprises one of monitoring a hand gesture in a clockwise motion, monitoring a hand gesture in a counter-clockwise motion, monitoring a hand gesture in a left-right motion, or monitoring a hand gesture in an up-down motion.

16. The system of claim 15, wherein the computerized processor further includes programming to:
monitor a confirmation to the monitored hand gesture input; and
control the voltage supplied to the tattoo machine further based upon the monitored confirmation.

* * * * *